(12) United States Patent
Fukuyo et al.

(10) Patent No.: US 10,260,997 B2
(45) Date of Patent: Apr. 16, 2019

(54) MICROORGANISM CONCENTRATOR

(71) Applicant: Satake Corporation, Tokyo (JP)

(72) Inventors: Yasuo Fukuyo, Chiba (JP); Yukio Hosaka, Hiroshima (JP); Akira Eto, Hiroshima (JP); Akiko Nakata, Hiroshima (JP)

(73) Assignee: SATAKE CORPORATION, Tokyo (JP)

( * ) Notice: Subject to any disclaimer, the term of this patent is extended or adjusted under 35 U.S.C. 154(b) by 0 days.

(21) Appl. No.: 14/902,037

(22) PCT Filed: Jul. 2, 2014

(86) PCT No.: PCT/JP2014/067648
§ 371 (c)(1),
(2) Date: Dec. 30, 2015

(87) PCT Pub. No.: WO2015/002229
PCT Pub. Date: Jan. 8, 2015

(65) Prior Publication Data
US 2016/0370261 A1 Dec. 22, 2016

(30) Foreign Application Priority Data
Jul. 5, 2013 (JP) .................. 2013-141325

(51) Int. Cl.
*G01N 1/10* (2006.01)
*C12Q 1/24* (2006.01)
(52) U.S. Cl.
CPC ............... *G01N 1/10* (2013.01); *C12Q 1/24* (2013.01); *G01N 2001/1025* (2013.01)

(58) Field of Classification Search
CPC .......... G01N 1/10; G01N 1/20; G01N 1/2021; G01N 1/1012; G01N 2001/1025;
(Continued)

(56) References Cited

U.S. PATENT DOCUMENTS 4,830,747 A * 5/1989 Kubota ................. B01D 29/15
134/22.12
6,409,914 B1 * 6/2002 Keppeler ............... C02F 3/1242
210/151

(Continued)

FOREIGN PATENT DOCUMENTS

CN 1126629 A 7/1996
CN 1555418 A 12/2004
(Continued)

OTHER PUBLICATIONS

Written Opinion for PCT/JP2014/067648 dated Sep. 9, 2014.
(Continued)

*Primary Examiner* — Nam X Nguyen
*Assistant Examiner* — Julia L. Wun
(74) *Attorney, Agent, or Firm* — Isshiki International Law Office; Joseph P. Farrar, Esq.

(57) ABSTRACT

A microorganism concentrator includes a water storage part that stores water sample therein and a filter that partitions the water storage part into a supply side and a drain side for the water sample. The microorganism concentrator concentrates microorganisms that are too large to pass through the filter on the supply side by moving the water sample on the supply side to the drain side of the water storage part. In the microorganism concentrator, the filter is arranged in such a way that no vertically downward force is applied to a surface of the filter on the supply side.

3 Claims, 4 Drawing Sheets

(58) Field of Classification Search
CPC .......... C12Q 1/24; B01D 29/00; B01D 29/01; B01D 29/0004; B01D 29/009; B01D 29/0095; B01D 2201/28; B01D 2201/48; B01D 2257/91; B01D 35/34; E02D 1/06; C02F 1/00; C12M 1/00; C12M 1/12
USPC ............ 210/422, 532.1, 534, 538, 540, 115, 210/170.1, 170.11, 902, 747.7, 747.5
See application file for complete search history.

(56) References Cited

U.S. PATENT DOCUMENTS

| | | | |
|---|---|---|---|
| 8,496,814 B2 * | 7/2013 | Kent | E03F 5/14 210/123 |
| 2005/0048474 A1 | 3/2005 | Amburgey | |
| 2012/0091067 A1 * | 4/2012 | Taylor | C12Q 1/24 210/740 |
| 2013/0183747 A1 | 7/2013 | Fukuda et al. | |
| 2014/0030803 A1 | 1/2014 | Hermet et al. | |
| 2014/0154731 A1 | 6/2014 | Halverson | |

FOREIGN PATENT DOCUMENTS

| | | |
|---|---|---|
| CN | 101693878 A | 4/2010 |
| CN | 201517105 U | 6/2010 |
| CN | 101842686 A | 9/2010 |
| CN | 101983328 A | 3/2011 |
| CN | 102316952 A | 1/2012 |
| CN | 102317754 A | 1/2012 |
| CN | 103771605 A | 5/2014 |
| JP | 60-24136 A | 2/1985 |
| JP | S63-37611 B2 | 7/1988 |
| JP | 01-258711 A | 10/1989 |
| JP | 1991-061869 | 6/1991 |
| JP | H05-240861 A | 9/1993 |
| JP | H07-001973 Y | 1/1995 |
| JP | H03-061869 U | 9/1999 |
| JP | 2001-252682 A | 9/2001 |
| JP | 3561460 B2 | 9/2004 |
| JP | 2005-261343 A | 9/2005 |
| JP | 2009-115500 A | 5/2009 |
| JP | 4469198 B2 | 5/2010 |

OTHER PUBLICATIONS

International Preliminary Report for PCT/JP2014/067648 dated Jan. 5, 2016.
International Search Report for Application No. PCT/JP2014/067648 dated Sep. 9, 2014.
Extended European Search Report for Application No. EP14820032 dated Jan. 17, 2017.
Taiwanese Office Action for Application No. 103123232 dated Dec. 20, 2017.

* cited by examiner

MICROORGANISM CONCENTRATOR

CROSS-REFERENCE TO RELATED APPLICATION

The present application is a national phase entry under 35 U.S.C. § 371 of International Application No. PCT/JP2014/067648, filed Jul. 2, 2014, which claims priority from Japanese Application No.: 2013-141325, filed Jul. 5, 2013, all of which are incorporated herein by reference.

BACKGROUND OF THE INVENTION

Technical Field

The present invention relates to a concentrator for microorganisms existing in water, and, for example, relates to a microorganism concentrator that can recover microorganisms in a living state included in ballast water, river water, or the like.

Background Art

To check the number of microorganisms in a living state included in ballast water, devices for concentrating microorganisms existing in the ballast water have been proposed (for example, see Patent Literature 1).

FIG. 4 illustrates a microorganism concentrating device that is disclosed by Patent Literature 1.

In the device disclosed by Patent Literature 1, a filter cloth 303 in a substantially inverted cone shape is set in a water storage container 300, a space 300A outside the filter cloth 303 is separated from a space 300B inside the filter cloth 303, an overflow pipe 312 and a drain port 313 are placed in the space 300A outside the filter cloth 303, and a lower-end opening 303b of the filter cloth 303 is connected with a reservoir 304.

According to the device disclosed by Patent Literature 1, when supply of sample water to the inside of the filter cloth 303 is continued, water in the water storage container 300 overflows from the overflow pipe 312 so that the sample water W2 moves from the inside to the outside of the filter cloth 303. Consequently, the number of aquatic organisms that are too large to pass through the filter cloth 303 increases in the space 303B inside the filter cloth 303.

After a predetermined amount of the sample water is supplied to the inside of the filter cloth 303 and the supply of the sample water is stopped, water in the water storage container 300 is drained from the outlet 313. Accordingly, the sample water moves from the inside to the outside of the filter cloth 303 to be drained from the drain port 313 so that concentrated water W3 including concentrated aquatic organisms that are too large to pass through the filter cloth 303 is stored in the reservoir 304 in the space 303B inside the filter cloth 303.

In the device disclosed by Patent Literature 1, when sample water moves from the inside to the outside of the filter cloth 303, aquatic organisms that are too large to pass through the filter cloth 303 hit against the inner surface of the filter cloth 303 and adhere to the inner surface of the filter cloth 303.

Pressure due to the movement of the sample water is applied to the aquatic organisms adhering to the inner surface of the filter cloth 303. However, since the filter cloth 303 has a substantially inverted cone shape that is a tapered shape, pressure of the self-weight in a vertically downward direction is further applied to the aquatic organisms.

Consequently, in the device disclosed by Patent Literature 1, aquatic organisms adhering to the inner surface of the filter cloth 303 are considerably damaged. Therefore, there is a possibility that most of the aquatic organisms die and cannot be recovered in a living state.

CITATION LIST

Patent Literature

Patent Literature 1: Japanese Patent Laid-Open No. 2009-115500

SUMMARY OF THE INVENTION

Technical Problem

Therefore, an object of the present invention is to provide a microorganism concentrator that can recover microorganisms existing in water in a living state.

Solution to Problem

To achieve the above object, a microorganism concentrator according to the present invention includes a water storage part that stores water sample therein and a filter that partitions the water storage part into a supply side and a drain side for the water sample, and the microorganism concentrator concentrates microorganisms that are too large to pass through the filter on the supply side by moving the water sample on the supply side to the drain side of the water storage part, wherein the filter is arranged in such a way that no vertically downward force is applied to a surface of the filter on the supply side.

On the drain side of the water storage part, preferably, an overflow part is placed at a position above the filter and a drain part is placed at a position below the lower end of the filter.

Preferably, a reservoir in which concentrated water including concentrated microorganisms that are too large to pass through the filter is stored is placed at a lower position on the supply side of the water storage part and a concentrated-water drain part for draining the concentrated water is placed in the reservoir.

Preferably, the filter has a substantially planar shape and the filter is arranged in such a way that the surface of the filter on the supply side is directed to a downward direction at an inclined angle of 0 to 90 degrees relative to a vertical surface.

Advantage Effects of Invention

In the microorganism concentrator according to the present invention, the filter that partitions the water storage part storing water sample therein into the supply side and the drain side for the water sample is arranged in such a way that no vertically downward force is applied to the surface of the filter on the supply side. Thus, even when microorganisms adhere to the inner surface of the filter on the supply side, no pressure of the self-weight is applied to the microorganisms so that most of the microorganisms can be recovered in a living state without receiving considerable damage.

On the drain side of the water storage part, when the overflow part is placed at a position above the filter and the drain part is placed at a position below the lower end of the filter, a wide range of the filter can be used effectively in moving the water sample from the supply side to the drain side of the water storage part.

After the drainage of water sample in the water storage part, concentrated water including concentrated microorganisms that are too large to pass through the filter remains on the supply side of the water storage part. However, when the drain part is placed at a position below the lower end of the filter, the amount of the concentrated water can be adjusted by the height position of the lower end of the filter.

When the reservoir in which the concentrated water is stored is placed at a lower position on the supply side of the water storage part and the concentrated-water drain part for draining the concentrated water is placed in the reservoir, the concentrated water stored in the reservoir can be recovered easily.

DETAILED DESCRIPTION OF EMBODIMENTS OF THE INVENTION

An embodiment of the present invention will be described with reference to the drawings. In the present embodiment, a case where plankton existing in ballast water is concentrated will be described as an example.

Figure 1:
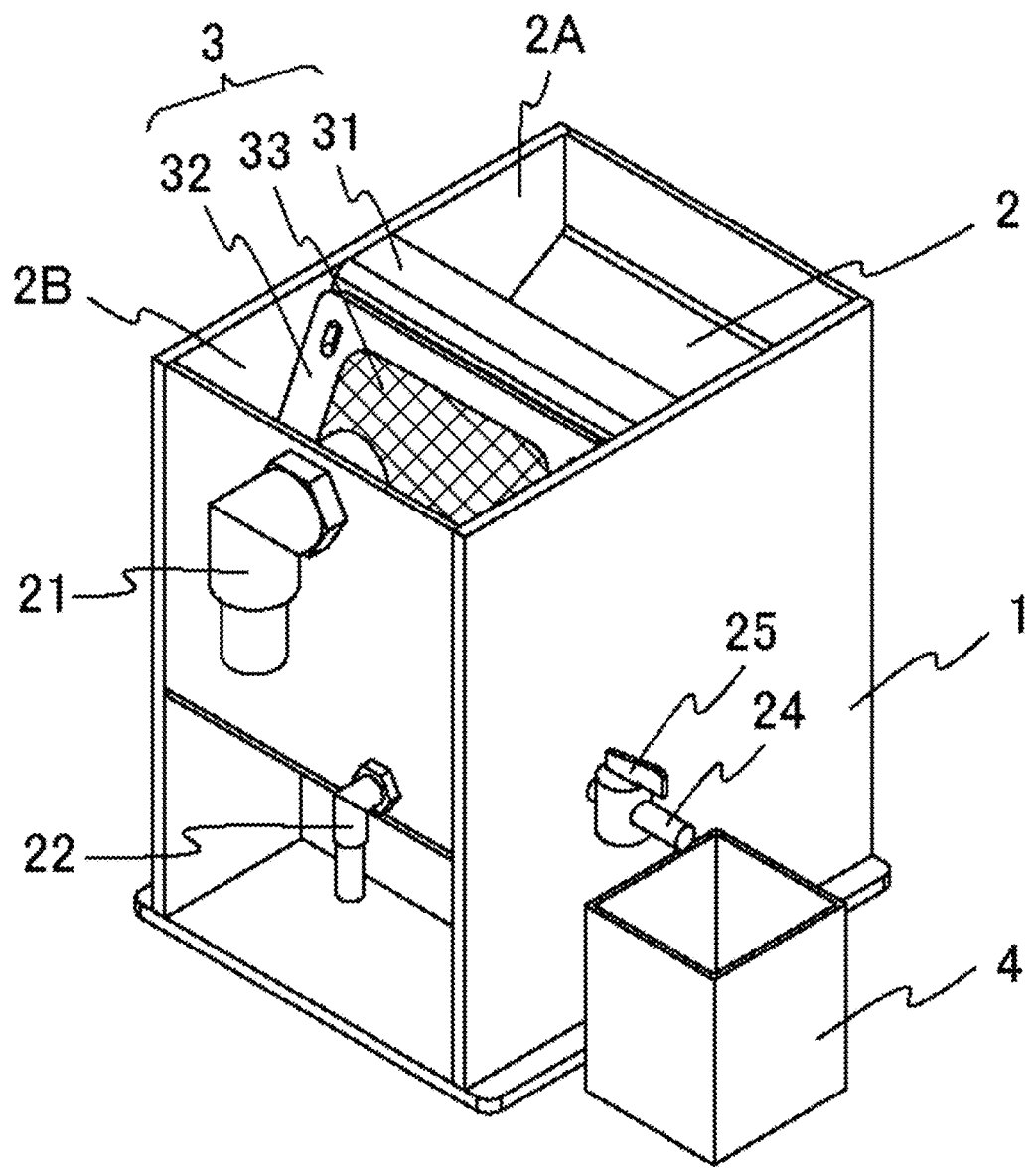
FIG. 1 is an overall perspective view of a microorganism concentrator of an embodiment of the present invention.
Figure 2:
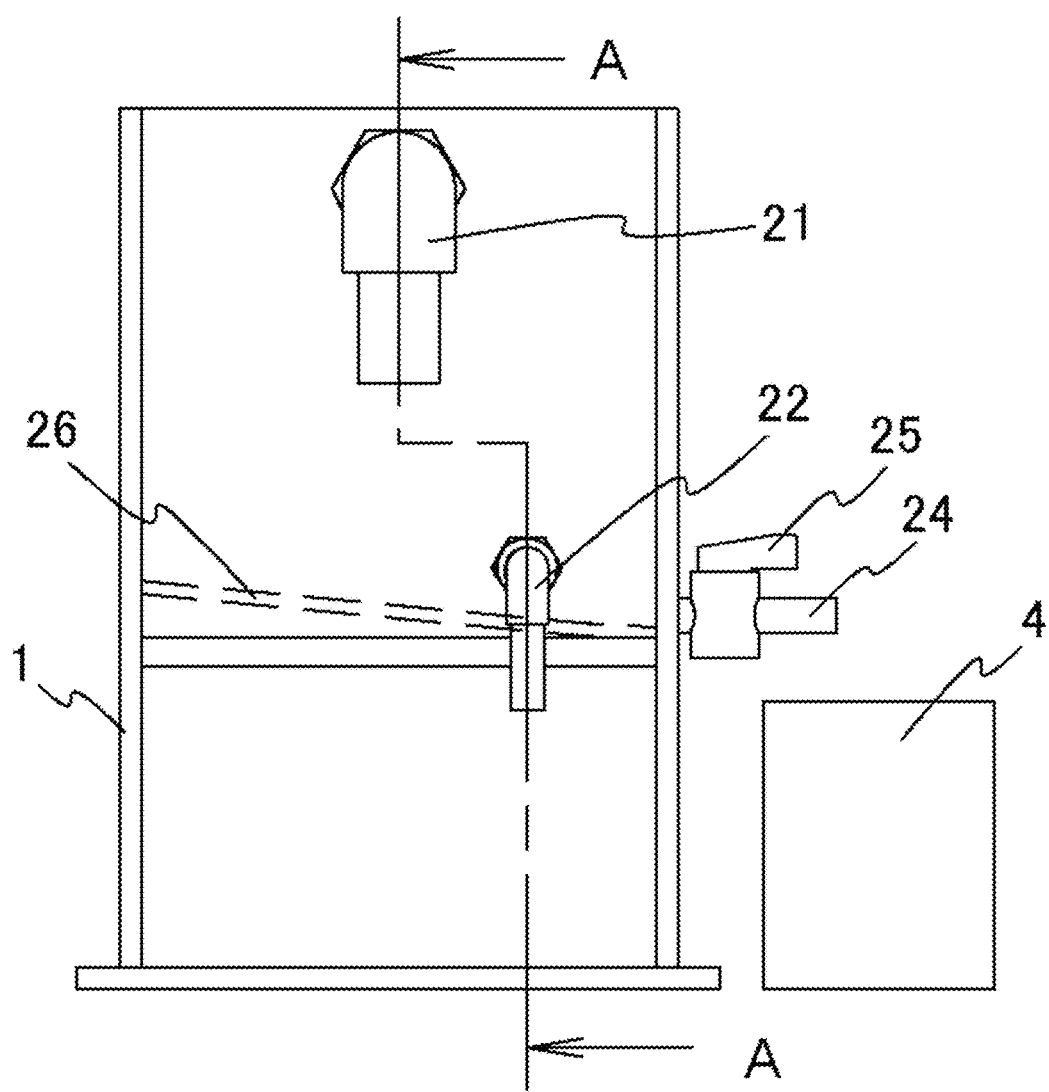
FIG. 2 is a front view of the microorganism concentrator of the embodiment of the present invention.
Figure 3:
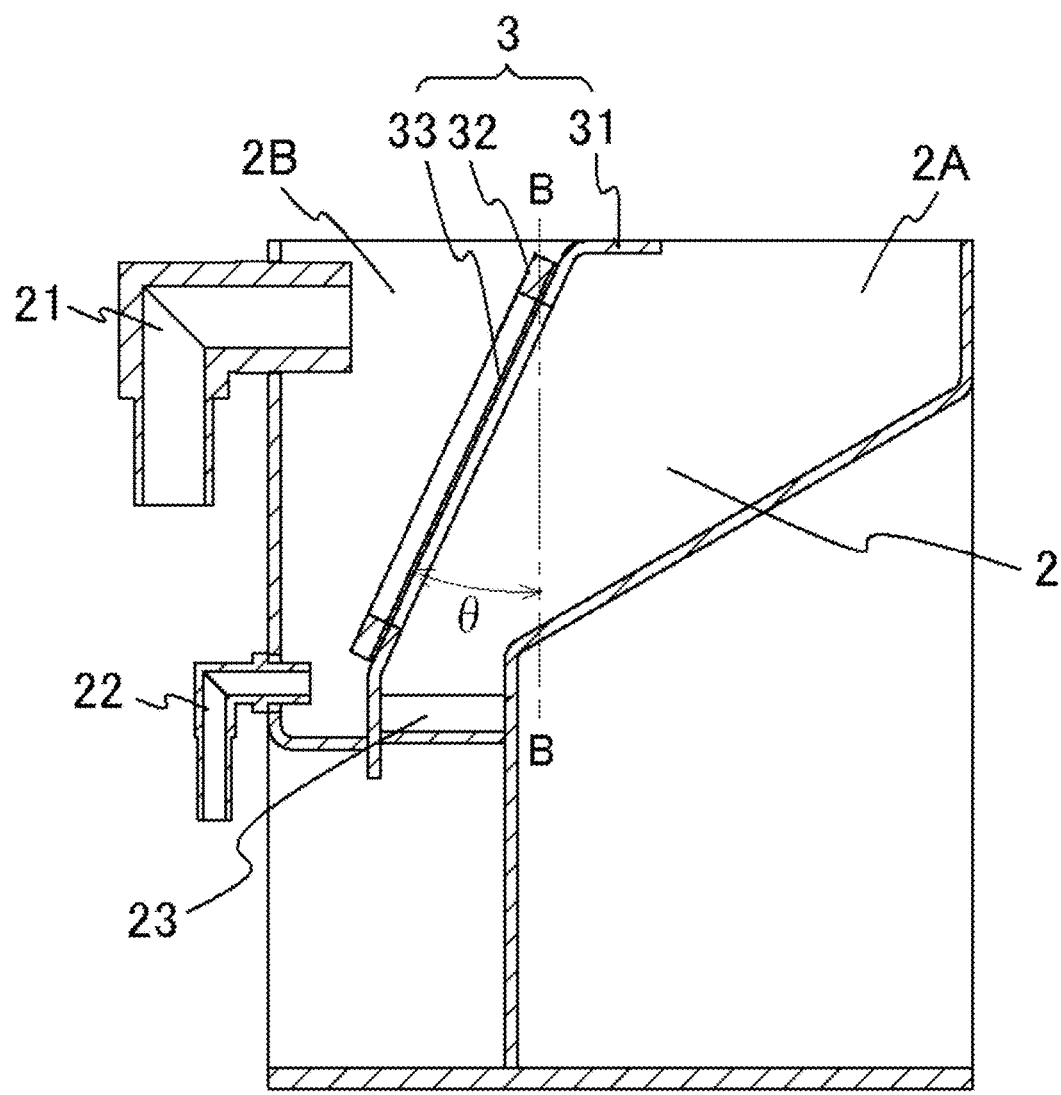
FIG. 3 is a sectional view taken along line A-A in FIG. 2.
Figure 4:
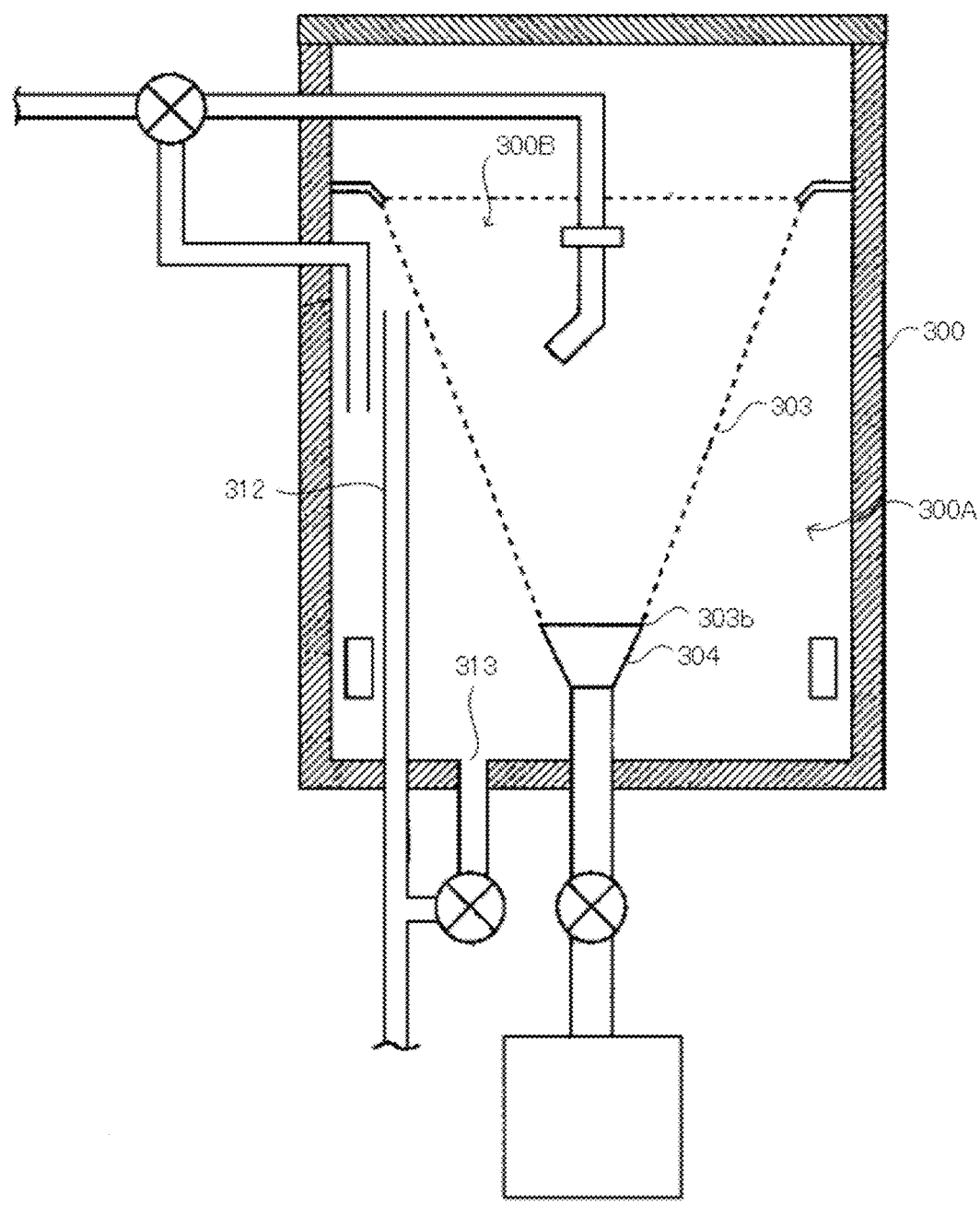
FIG. 4 is an explanatory view of a microorganism concentrating device disclosed in Patent Literature 1.

FIG. 1 is an overall perspective view of a microorganism concentrator in the present embodiment. FIG. 2 is a front view of the microorganism concentrator in the present embodiment. FIG. 3 is a section view taken along line A-A in FIG. 2.

The microorganism concentrator in the present embodiment includes a water storage tank 2 that sample water taken from ballast water is stored as water sample in an inside of a concentrator main body 1. A filter member 3 partitions the inside of the water storage tank 2 into a sample-water supply side 2A and a sample-water drain side 2B.

The filter member 3 is formed of a partitioning frame 31 that is fixed in the water storage tank 2, a fixing frame 32 that is fixed on one surface of the partitioning frame 31 and sandwiches a net filter 33, which will be described later, between the partitioning frame 31 and the fixing frame 32, and the net filter 33 that has a planar shape and is sandwiched between the partitioning frame 31 and the fixing frame 32.

The net filter 33 is arranged in such a way that no vertically downward force is applied to the surface of the net filter 33 on the sample-water supply side 2A, that is, in such a way that the surface on the supply side 2A is directed to the downward direction at an inclination angle θ of 0 to 90 degrees relative to a vertical surface B-B, as illustrated in FIG. 3.

The net filter 33 here is arranged at the inclined angle θ of approximately 30 degrees relative to the vertical surface B-B with the surface on the supply side 2A directed to the downward direction.

A net filter formed of warp and weft intersecting in a grid pattern may be used as the net filter 33. It suffices that the size of the grid of the net filter 33 prevents passing of plankton that has a size to be recovered. For example, a net filter with a 50-μm diagonal line of the grid is used.

An overflow gutter 21 is placed on the upper part of the front surface on the sample-water drain side 2B in the water storage tank 2. When supply of sample water to the water storage tank 2 is continued, sample water stored in the water storage tank 2 overflows from the overflow gutter 21. Thus, a level of sample water stored in the water storage tank 2 can be kept constant.

A drain gutter 22 is placed at a position that is in the lower part of the front surface on the drain side 2B in the water storage tank 2 and is lower than the lower end of the net filter 33. Sample water stored in the water storage tank 2 can be drained from the drain gutter 22 by opening a valve (not illustrated).

On the other hand, a reservoir 23 in which concentrated water including concentrated plankton that is too large to pass through the net filter 33 is stored is placed at a position below the lower end of the net filter 33 on the sample-water supply side 2A of the water storage tank 2.

A concentrated-water drain gutter 24 is placed on the side surface of the reservoir 23. A faucet 25 is provided to the concentrated-water drain gutter 24. The concentrated water can be drained to a concentrated-water container 4 by opening the faucet 25.

As illustrated in FIG. 2, a bottom 26 of the reservoir 23 has an inclination in such a way that one side provided with the concentrated-water drain gutter 24 is lower than the other, so as to have a structure in which concentrated water stored in the reservoir 23 can be drained easily from the concentrated-water drain gutter 24.

Next, to explain the operation of the microorganism concentrator in the present embodiment, a case where plankton existing in ballast water is concentrated will be described as an example.

While the valve of the drain gutter 22 and the faucet of the concentrated-water drain gutter 24 are closed, sample water taken from ballast water is supplied as water sample to the supply side 2A of the water storage tank 2.

When supply of the sample water to the supply side 2A of the water storage tank 2 is continued, the water storage tank 2 gets to be filled with the sample water and the sample water stored in the water storage tank 2 overflows from the overflow gutter 21.

While the water level in the water storage tank 2 is kept constant by the overflow of the sample water stored in the water storage tank 2, supply of a necessary amount of the sample water is continued. Here, supply of the sample water is continued until an amount of the supplied water reaches 1 m³.

During the above supply, the sample water passes through the net filter 33 from the supply side 2A of the water storage tank 2 and moves to the drain side 2B.

After the necessary amount of sample water is supplied, the valve of the drain gutter 22 is opened to drain the sample water stored in the water storage tank 2 from the drain gutter 22.

At that time, the sample water on the supply side 2A of the water storage tank 2 passes through the net filter 33 to move to the drain side 2B, and is drained from the drain gutter 22.

After the sample water is drained from the drain gutter 22, concentrated water remains in the reservoir 23 on the supply side 2A while plankton with a size of 50 μm or more, which cannot pass through the net filter 33, is concentrated in the concentrated water.

Plankton that adheres to the net filter 33 after the drainage of sample water from the drain gutter 22 can be dropped into the reservoir 23 by appropriate means such as spraying ballast water from the drain side 2B of the net filter 33.

The concentrated water stored in the reservoir 23 is drained from the concentrated-water drain gutter 24 to the concentrated-water container 4 by opening the faucet 25.

The concentrated water recovered into the concentrated-water container 4 includes plankton that has existed in 1 m³ of ballast water in a living state.

In the above descriptions, sample water is supplied to the water storage tank 2 while the valve of the drain gutter 22 is closed. However, sample water may be supplied to the water storage tank 2 while the valve of the drain gutter 22 is opened.

In the microorganism concentrator in the present embodiment, the net filter 33 is arranged at the inclined angle θ of approximately 30 degrees relative to the vertical surface B-B in such a way that the surface of the net filter 33 on the sample-water supply side 2A in the water storage tank 2 is directed to the downward direction.

Consequently, according to the microorganism concentrator in the present embodiment, when the sample water moves from the supply side 2A to the drain side 2B in the water storage tank 2, no pressure of the self-weight is applied to plankton adhering to the surface of the net filter 33 on the supply side 2A. Thus, the plankton can be recovered in a living state without receiving considerable damage.

Furthermore, in the microorganism concentrator in the present embodiment, the overflow gutter 21 is placed at a position above the net filter 33 and the drain gutter 22 is placed at a position below the lower end of the net filter 33.

Consequently, according to the microorganism concentrator in the present embodiment, when sample water moves from the supply side 2A to the drain side 2B in the water storage tank 2, a wide range of the net filter 33 can be used effectively.

Alternatively, the overflow gutter 21 in the present embodiment may be placed at a position above the upper end of the net filter 33. When the overflow gutter 21 is placed at a position above the upper end of the net filter 33, the whole surface of the net filter 33 can be used effectively.

Moreover, in the microorganism concentrator in the present embodiment, after the drainage of sample water in the water storage tank 2, concentrated water remains on the supply side 2A of the water storage tank 2 while plankton that is too large to pass through the net filter 33 is concentrated in the concentrated water. However, since the drain gutter 22 is placed at a position below the lower end of the net filter 33, the amount of the concentrated water can be adjusted by the height position of the lower end of the net filter 33.

In the present embodiment, the filter member 3 is formed using the net filter 33 that has a planar shape. However, the shape of the net filter 33 is not limited to a planar shape. For example, a net filter that has a curved shape can be used as long as the net filter can be arranged in such a way that no vertically downward force is applied to the surface of the net filter on the sample-water supply side 2A in the water storage tank 2.

In the present embodiment, a case where plankton existing in ballast water is concentrated has been described as an example. However, the microorganism concentrator in the present embodiment can be used also to concentrate microorganisms existing in other types of water such as river water and sewage water.

The present invention is not limited to the present embodiment. As a matter of course, the configuration of the present invention can be appropriately modified within the scope of the invention.

INDUSTRIAL APPLICABILITY

The present invention allows recovery of microorganisms existing in water in a living state such as ballast water and river water. Thus, the present invention has a high practical value.

REFERENCE SIGNS LIST 1 concentrator main body
2 water storage tank
2A supply side
2B drain side
21 overflow gutter
22 drain gutter
23 reservoir
24 concentrated-water drain gutter
25 faucet
26 bottom
3 filter member
31 partitioning frame
32 fixing frame
33 net filter
B-B vertical surface

The invention claimed is:

1. A microorganism concentrator comprising:
a water storage part to which a sample of water taken from ballast water is supplied from above as a water sample and is stored therein; and
a filter that partitions the water storage part into a supply side and a drain side,
the microorganism concentrator concentrating microorganisms that are too large to pass through the filter on the supply side by moving the water sample on the supply side to the drain side of the water storage part defined within a body of the concentrator,
wherein the filter is arranged in such a way that no vertically downward force is applied to microorganisms adhered upon filtration to a surface of the filter on the supply side,
wherein, on the drain side of the water storage part, an overflow part is placed at a position above the filter and a drain part is placed at a position below a lower end of the filter, the overflow part and the drain part extending outward from the body of the concentrator,
wherein a reservoir in which concentrated water including concentrated microorganisms that are too large to pass through the filter is stored is disposed at a lower position within the supply side that is adjacent to the drain side of the water storage part, and a concentrated-water drain part extending outward from a side surface of the body of the concentrator for draining the concentrated water is placed in the reservoir,
wherein a bottom of the supply side of the storage part forms a single unbroken plane inclined downward in a direction from one end of the supply side of the storage part toward an opposite end of the storage part near the reservoir, and
wherein the filter is inclined upward at an angle and in a direction orthogonal to the inclination direction of the bottom of the supply side,
wherein a lower end of the filter determines a capacity of the reservoir,
wherein the filter has a substantially planar shape, and the filter is arranged in such a way that the surface of the filter on the supply side is at an inclined angle of from 0 to 90 degrees relative to a vertical surface, wherein the capacity of the reservoir can be adjusted by a height position of the lower end of the filter;

wherein a bottom of the reservoir is inclined downwardly in a direction toward the concentrated-water drain part, and the inclination direction of the bottom of the supply side of the storage part is in the flow direction of the sample water and orthogonal to the inclination direction of the bottom of the reservoir.

2. The microorganism concentrator according to claim 1, wherein the filter is sandwiched between a partitioning frame, which partitions the water storage tank into a water sample supply side and a water sample drain side, and a fixing frame.

3. The microorganism concentrator according to claim 1, wherein the filter is a screen having a mesh size sufficient to prevent passage of microorganisms from the supply side to the drain side of the water storage part defined within the body of the microorganism concentrator.

* * * * *